(12) United States Patent
Leblanc et al.

(10) Patent No.: US 11,364,554 B2
(45) Date of Patent: Jun. 21, 2022

(54) PARABOLIC INSTRUMENT

(71) Applicant: DENTSPLY SIRONA Inc., York, PA (US)

(72) Inventors: Romain Leblanc, Jougne (FR); Eric Bourque, Granges Narboz (FR)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 15/939,361

(22) Filed: Mar. 29, 2018

(65) Prior Publication Data

US 2018/0281085 A1   Oct. 4, 2018

Related U.S. Application Data

(60) Provisional application No. 62/478,350, filed on Mar. 29, 2017.

(51) Int. Cl.
| | |
|---|---|
| *B23B 51/02* | (2006.01) |
| *A61B 17/16* | (2006.01) |
| *A61C 8/00* | (2006.01) |
| *A61C 3/00* | (2006.01) |

(52) U.S. Cl.
CPC .......... *B23B 51/02* (2013.01); *A61B 17/1615* (2013.01); *A61B 17/1673* (2013.01); *A61C 3/00* (2013.01); *A61C 8/0089* (2013.01); *B23B 2251/043* (2013.01); *B23B 2251/08* (2013.01); *B23B 2251/12* (2013.01); *B23B 2251/40* (2013.01)

(58) Field of Classification Search
CPC .............. B23B 51/02; B23B 2251/241; B23B 2251/245; B23B 2251/043; B23B 2251/44; B23B 2251/08; B23B 2251/12; B23B 2251/40; B23C 2210/241; Y10T 408/854; A61C 3/02; A61C 8/0089; A61C 3/00; A61B 17/1673; A61B 17/1615
USPC .................................................. 433/165, 166
See application file for complete search history.

(56) References Cited

U.S. PATENT DOCUMENTS

| | | | | |
|---|---|---|---|---|
| 374,432 | A | * | 12/1887 | Simmons ............... B27G 15/00 408/213 |
| 2,897,695 | A | * | 8/1959 | Winslow ............... B23B 51/108 408/223 |
| 4,231,693 | A | * | 11/1980 | Kammeraad .......... B23D 77/00 29/401.1 |
| 5,380,133 | A | * | 1/1995 | Schimmer ............... B23B 51/02 408/199 |

(Continued)

FOREIGN PATENT DOCUMENTS

JP    2003053611 A  *  2/2003

OTHER PUBLICATIONS

International Search Report; PCT/US2018/024995; May 30, 2018 (completed); dated Jun. 11, 2018.

(Continued)

*Primary Examiner* — Chwen-Wei Su
(74) *Attorney, Agent, or Firm* — Dentsply Sirona Inc.

(57) ABSTRACT

An instrument comprising a shank and a working portion, the working portion having a tip and a plurality of flutes being defined by at least two lands having a land margin; wherein the working portion has a parabolic cross-section defining opposing convexed surfaces extending between at least two opposing land margins.

12 Claims, 12 Drawing Sheets

(56) References Cited

U.S. PATENT DOCUMENTS

| | | | | |
|---|---|---|---|---|
| 5,876,202 | A * | 3/1999 | Berlin | A61C 3/02 |
| | | | | 408/230 |
| 6,250,857 | B1 * | 6/2001 | Kersten | B23B 51/02 |
| | | | | 175/394 |
| 6,443,674 | B1 * | 9/2002 | Jaconi | B23B 51/02 |
| | | | | 408/1 R |
| 6,602,029 | B1 * | 8/2003 | George | B23B 51/02 |
| | | | | 407/23 |
| 8,226,654 | B2 * | 7/2012 | Ranck | A61B 17/1615 |
| | | | | 606/167 |
| 2002/0141842 | A1 * | 10/2002 | Tsuzaka | B23B 51/02 |
| | | | | 408/230 |
| 2003/0159544 | A1 * | 8/2003 | Moser | B21C 23/147 |
| | | | | 76/108.6 |
| 2015/0056032 | A1 * | 2/2015 | Scianamblo | B23B 51/0081 |
| | | | | 408/1 R |
| 2016/0228130 | A1 | 8/2016 | Koljaka | |

OTHER PUBLICATIONS

International Preliminary Report on Patantablity; PCT/US2018/024995; May 30, 2018 (completed); dated Jun. 11, 2018.
Written Opinion of the International Searching Authority; PCT/US2018/024995; May 30, 2018 (completed); dated Jun. 11, 2018.

* cited by examiner

FIG. 4B
Section A-A

FIG. 4C
Section B-B

FIG. 4D
Section C-C

FIG. 4E
View F

Version 1
Helix angle 28°
base 5°
Parallel web 0.7 mm
Web thinning 0.15 mm
Tip angle 118°

FIG. 7A

Version 2
Helix angle 30°
base 7°
Parallel web 1.0mm
Web thinning 0.15 mm
Tip angle 118°

Opening Angle      3D view

FIG. 10A

Opening Angle      3D view

FIG. 10B

Opening Angle      3D view

FIG. 10C

Opening Angle      3D view

Twist drill Ø2.2 L33mm

Twist drill Ø2.2 L33mm - Parabolic

Twist drill Ø2.8 L33mm

Twist drill Ø2.8 L33mm - Parabolic

Twist drill Ø4.2 L33mm

Twist drill Ø4.2 L33mm - Parabolic

PARABOLIC INSTRUMENT

THE CROSS-REFERENCE TO RELATED APPLICATIONS

This patent application claims the benefit of and priority to U.S. Provisional Application Ser. No. 62/478,350, filed on Mar. 29, 2017, which is herein incorporated by reference for all purposes.

TECHNICAL FIELD

The present invention relates to the field of drill bits, more particularly the field of medical and/or dental drills/files.

BACKGROUND OF THE INVENTION

The prior art drill bit designs can result in blockage of the flutes during the drilling. This issue is not due to the cutting efficiency, but directly correlated by the lack of space which is available for the bone chips removing. It means that the surgeons must stop the drilling, move out the drill and remove manually the bone chips. In addition, if bone chips are not correctly removed during the drilling, the friction (torque) will be more important and the thermal effect too. As a consequence, the risk of osteonecrosis will be higher and the osteo-integration of the implant could be compromised.

OBJECT OF THE INVENTION

It is an object of the present invention to substantially overcome or at least ameliorate at least one of the above disadvantages.

SUMMARY OF THE INVENTION

In a first aspect the present invention provides An instrument comprising a shank and a working portion, the working portion having a tip and a plurality of flutes being defined by at least two lands having a land margin; wherein the working portion has a parabolic cross-section defining opposing convexed surfaces extending between at least two opposing land margins.

In yet another aspect, any of the aspects of the present invention may be further characterized by one or any combination of the following features: each land margin is defined by a width W and the core is defined by a thickness T so that the width W of at least one land margin is smaller than the thickness T of the core; the width W of each land margin is smaller than the thickness T of the core; the width W ranges from 0.03 mm to 1.8 mm; the thickness T ranges from about 0.1 mm to about 2.0 mm; at least one of the plurality of flutes include a helical angle ranging from about 15° to about 50°; each of the plurality of flutes include a helical angle ranging from about 15° to about 50°; further comprising an opening angle φ of the plurality of flutes ranging from 91° to 179°, the opening angle φ is determined between two diametrical reference lines RL1 and RL2, which are situated in one and the same plane perpendicular to a center axis A, with RL1 extending between a leading edge region of a first land and the center axis A and RL2 extending between a trailing edge region of a second land and the center axis A; the instrument is an implant drill; or any combination thereof.

In substantially any said working portion cross-sectional plane, said convexly curved land leading edge region may be defined by a plurality of discrete chamfered surfaces.

BRIEF DESCRIPTION OF THE DRAWINGS

Preferred embodiments of the present invention will now be described, by way of example only, with reference to the accompanying drawings wherein.

DETAILED DESCRIPTION OF THE PREFERRED EMBODIMENTS

"Parabolic" instruments (e.g.,drills and/or files) are intended to be used by certified dental practitioners for the shaping and removal of bone before placing a dental implant. The instrument will be made of different materials such as High Speed Steel, Stainless steel, Stainless steel+ medical coating (AlTiN, DLC, TiN, etc.). It is appreciated that various kinds of stainless steel can be used for the parabolic/worm spiral drills of the present invention. According to the cutting performance assessed during this project, these drills proved to be a very good instrument for osteotomy. This instrument is to be used mechanically with current handpieces (contra-angle) used in implantology. The system will neither cover new indications nor use any new technology other than those used in currently marketed products.

It is believed that compared to current market drills, the innovative features of the parabolic/worm spiral drills of the present invention include, but are not limited to a convex web and the fast helix angle which allow to change the proportion of empty and full, by increasing significantly the empty. Thanks to that, a lot of space is available for removing bone chips, thus limiting friction. As a consequence, the risk of screw effect is diminished and thermal effect during drilling is reduced. Another feature of the present invention may include a high helix angle (fast spiral) which reduces the effect of lateral cut and favors the cylinder shape desired in osteotomy.

Referring to FIGS. 1, 2, 4A-4E, and 5 of the accompanying drawings, a drill bit 1 according to a first embodiment has a tapered cutting end part 2 terminating in a drill tip 3 at a front, operative end of the drill bit 1, with a shank 4 extending from an opposing rear end 4b of the drill bit 1. The opposing rear end 4b may be configured to be received within the chuck of a drill in the usual way. A working portion 4a of the drill bit 1 extends between the cutting end part 2 and the shank 4. A plurality of flutes 5 are formed in the drill bit 1. In the embodiment depicted there are three flutes 5 that each helically extend along the working portion 4a from adjacent the shank 4 into the cutting end part 2, although it is envisaged that the drill bit 1 may have only two flutes 5 or three or more flutes 5. Each of the flutes 5 extends into the cutting end part 2 towards the drill tip 3, but finishes just short of the drill tip 3 as a result of the tapering of the cutting end part 2.

In the embodiment depicted, the drill bit 1 is configured to be rotated in a clockwise direction when viewed from the rear of the drill bit 1. Throughout this specification, various features of the drill bit will be referred to as "leading" or "trailing", with this terminology indicating features that lead or trail respectively as the drill bit rotates in the intended manner. Each of the flutes 5 has a flute leading side wall 6 (which faces against the intended direction of rotation) and a flute trailing side wall 7 (which faces in the intended direction of rotation). The flute leading side wall 6 is joined to the flute trailing side wall 7 by way of a flute base 8 located therebetween. As best depicted in the cross-sectional views of FIG. 5, the flute leading side wall 6, flute base 8 and flute trailing side wall 7 effectively form a smooth continuous surface. The flutes 5 may be each formed with a helical angle of at least about 15°, preferably at least about 20°, and more preferably at least about 25°. Furthermore, the flutes 5 each may be formed with a helical angle of at most about 50°, preferably at most about 45°, and more preferably at most about 40°. For example, the flutes 5 each may be formed with a helical angle ranging from about 15° to about 50°, preferably from about 20° to about 45°, and more preferably from about 25° to about 40°.

The flute bases 8 extend to and define a core 13 having a web thickness T (e.g., diameter of core 13) of at least about 0.1 mm, preferably at least about 0.4 mm, and preferably at least about 0.7 mm. Furthermore, the core 13 may have a web thickness of at most about 2.0 mm, preferably at most about 1.7 mm, and more preferably at most about 1.4 mm. For example, the core 13 may have a web thickness T ranging from about 0.1 mm to about 2.0 mm, preferably from about 0.4 mm to about 1.7 mm, and more preferably from about 0.7 mm to about 1.4 mm. The core 13 extends along the central axis A having a constant web thickness T (e.g., Cylindrical and/or parallel web) or may include a slight taper (e.g., tapered web) of about 1 degree with respect to the central axis A of the drill bit, reducing or increasing the depth of the flutes 5 towards the shank 4 or tip 3. Typical taper angles will be between 0° and 5°. The taper may be constant or variable.

A land 9 is defined between each of the flutes 5. As best depicted in the cross-sectional view of FIG. 5, each land 9 may a land leading edge region 11 adjoining the adjacent flute trailing side wall 7 of the adjacent flute 5 directly leading the land 9. A land margin 10 is defined adjoining and trailing the land leading edge region 11. Moreover, the leading edge regions 11 may be cutting/scraping edges of the leading side wall 7.

Figure 1:
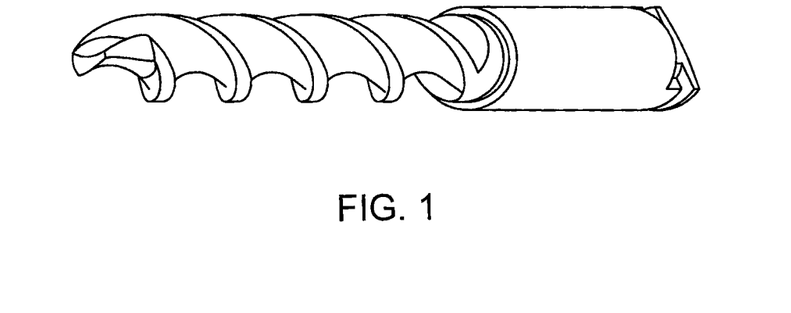
FIG. 1 is a perspective view of a first embodiment of the present invention.
Figure 2:
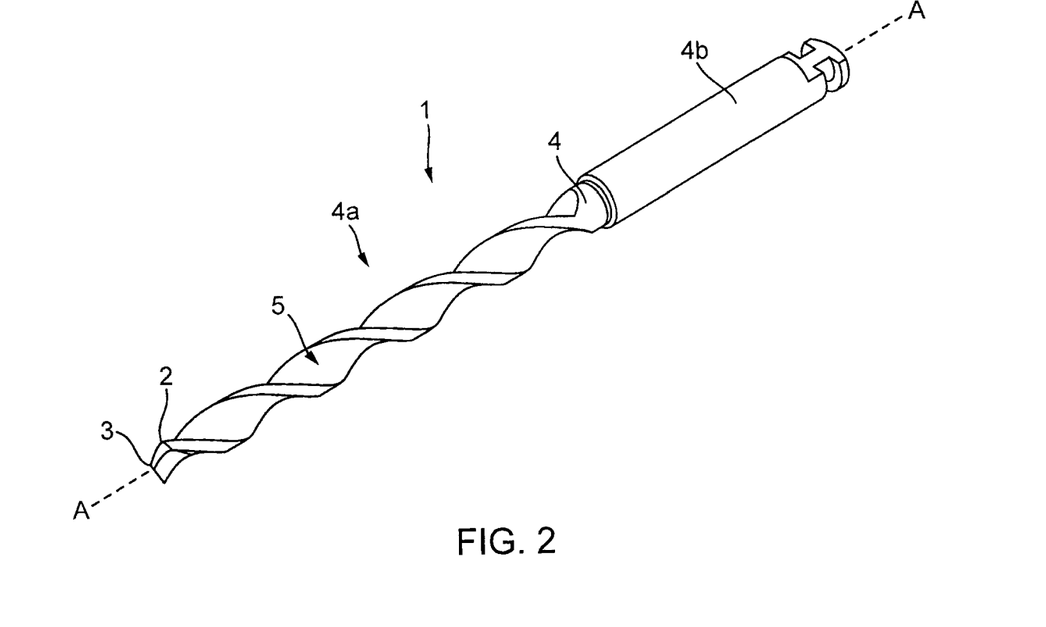
FIG. 2 is another perspective view of the first embodiment shown in FIG. 1.
Figure 3A:
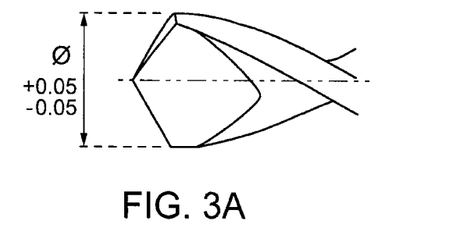
FIG. 3A is a partial view of the first embodiment shown in FIG. 1.
Figure 3B:
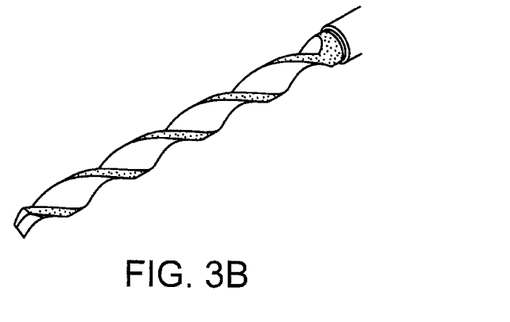
FIG. 3B is partial perspective view of the first embodiment shown in FIG. 1.
Figure 3C:
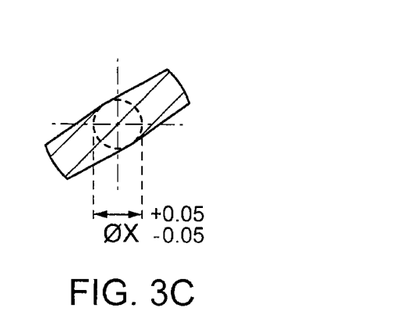
FIG. 3C is cross-sectional view of the first embodiment shown in FIG. 1.
Figure 3D:
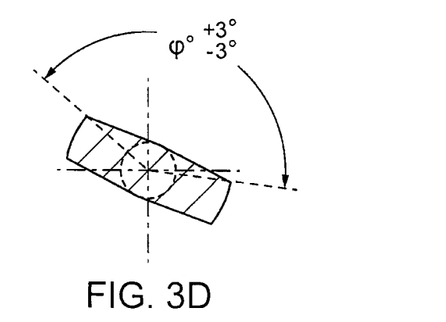
FIG. 3D is another cross-sectional view of the first embodiment shown in FIG. 1.
Figure 3E:
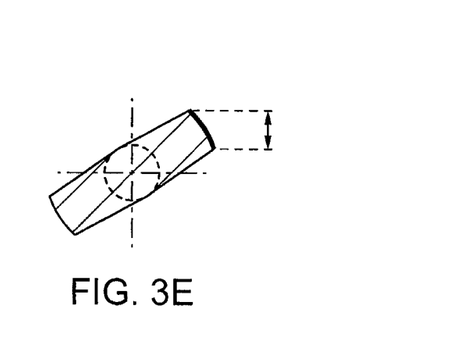
FIG. 3E is another cross-sectional view of the first embodiment shown in FIG. 1.
Figure 3F:
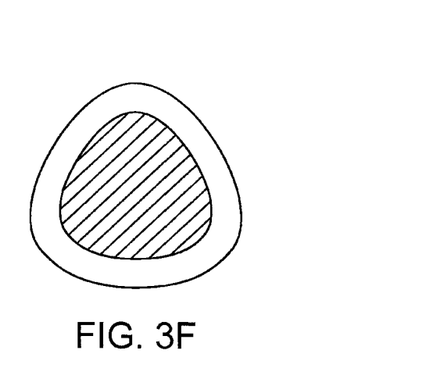
FIG. 3F is a cross-sectional view of the shank of the first embodiment shown in FIG. 1.
Figure 4A:
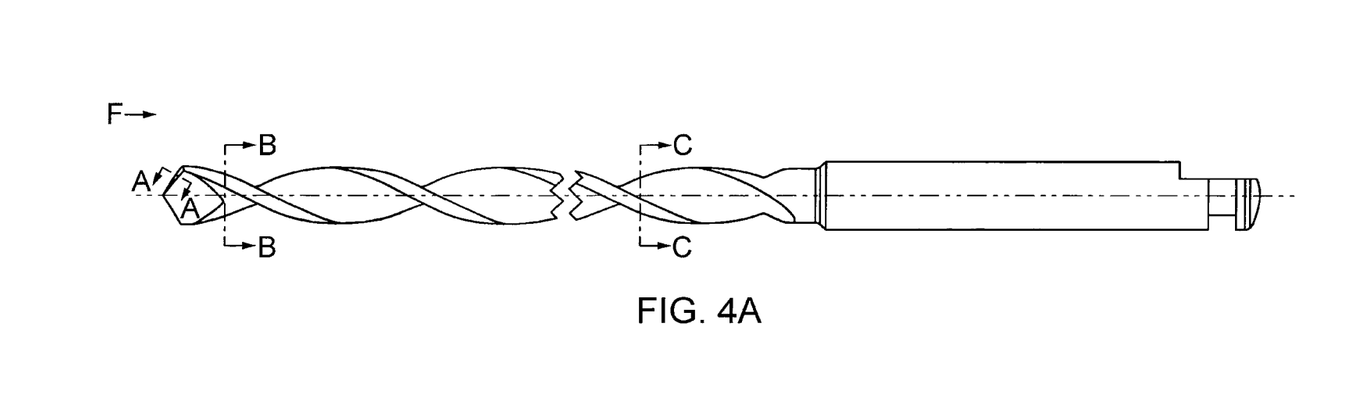
FIGS. 4A-4E show various views of a second embodiment of the present invention.
Figure 4B:
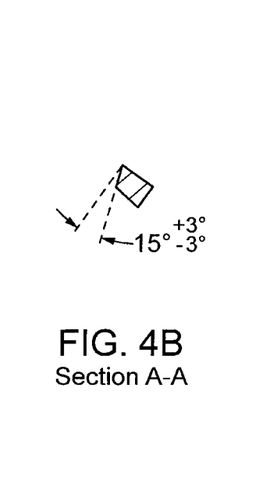
Figure 4C:
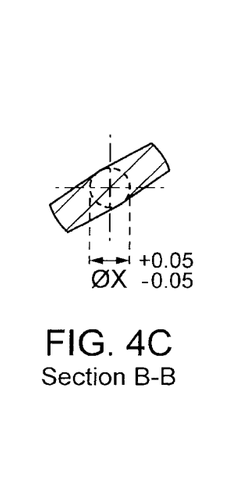
Figure 4D:
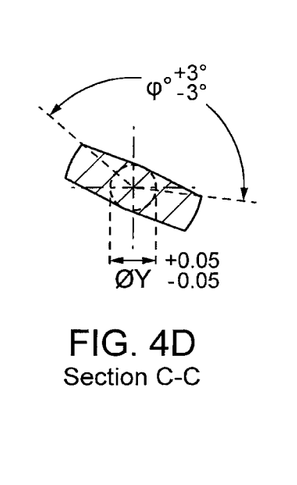
Figure 4E:
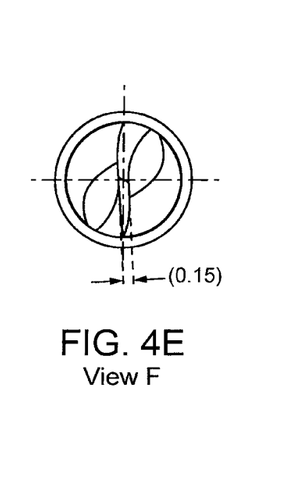
Figure 5:
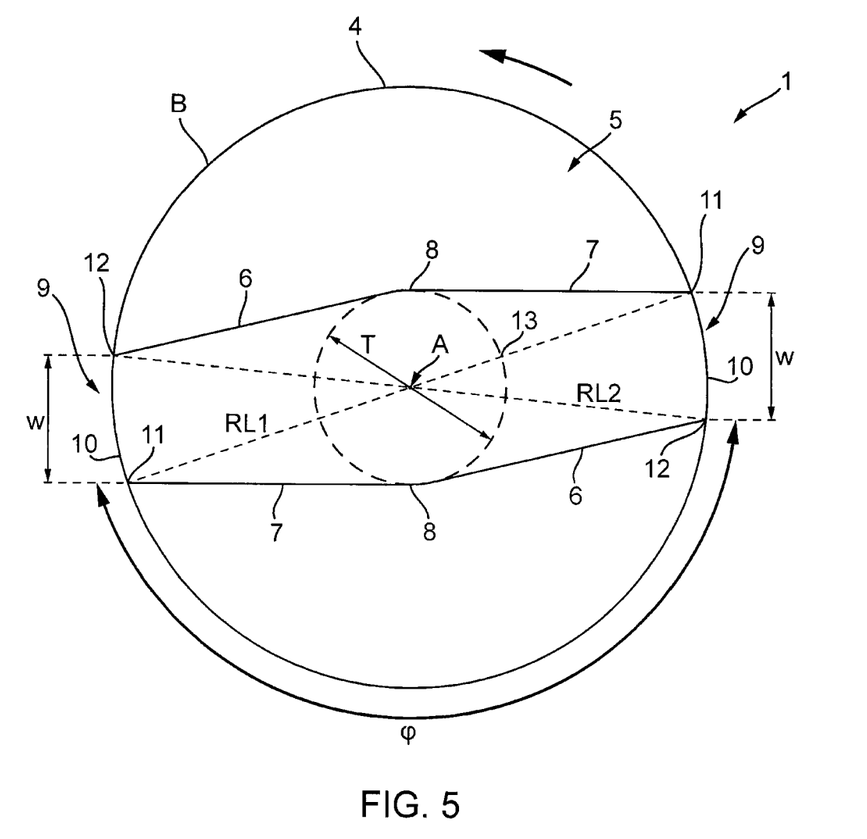
FIG. 5 is cross-sectional view of a third embodiment of the present invention.

The trailing side wall 6 and/or the leading side wall 7 may extend between the bases 8 and the trailing edge region 12 and/or the leading edge region 11, respectively of the opposed land margin 10 in a straight or arcuate manner such that the overall wall (e.g., trailing side wall 6 and the leading side wall 7 extending between the trailing edge region 12, the base 8 and the leading edge portion 11 define a generally convex configuration. As shown in FIG. 5, the trailing side wall 6 and the leading side wall 7 each define a generally straight side wall segment, however taken together, (e.g., extending between the trailing edge region 12, the base 8, and the leading edge portion 11), a generally convex cross-section may be defined. This may be contrasted to typical prior art drill bits that define a concavely curved edge at the intersection between the leading edge of each land and the adjacent flute trailing side wall.

As shown in FIGS. 10A-10D a thermal study between three two-fluted twist drills, which include improved parabolic designs of the present invention. The convex web and/or the fast helix angle of the present invention may allow for a change in the proportion of "empty" areas/spaces (e.g., flute areas) relative to the "full" areas/spaces (e.g., lands and core areas) by significantly increasing the "empty" areas. By increasing the "empty" areas, additional bone or tooth chips may be removed more easily as the hole is being created in the bone or tooth thereby reducing/limiting friction. As a consequence, the risk of screw effect is diminished and thermal effect during drilling is reduced.

The working portion 4a of the drill bit 1 may not be provided with any secondary cutting edge thereby leaving the entire cutting operation to the cutting end part 2, as will be described in further detail below. As a result, in the event that the operator moves the drill bit off-center during the drilling process, there will be less tendency for the drill hole to be cut and widened by the misaligned working portion of the drill bit as compared to where sharp secondary cutting edges are provided on the working portion. There is also a reduced possibility of damage to soft tissue in dental/ medical applications, reducing the possibility of the working portion of the drill bit biting into soft tissue and having soft tissue engaged and wrapped around the working portion. Providing a generally obtuse shaped land leading edge region on each land also improves the smoothness of operation of the drill bit, reducing the aggressiveness of engagement of the drill bit, enabling provision of a smooth cutting process under decreased torque. These benefits may also be achieved without adversely affecting the structural integrity of the drill bit, maintaining a significant moment of inertia of the drill bit by not needing to reduce the amount of material in the working portion of the drill bit at full diameter to accommodate a greater angle between the flute trailing face and land to soften a secondary cutting edge. The convex curvature of the land leading edge region 11 may be achieved with a plurality of discrete chamfered surfaces rather than a continuous curve.

The working portion 4a of the drill bit 1 may typically have an overall diameter of at least 1.0 mm, preferably at least 2.2 mm, and more preferably at least 3.4 mm. Furthermore, the working portion 4a may typically have an overall diameter of at most 8.0 mm, preferably at most 6.8 mm, and more preferably at most 5.6 mm. For example, the drill bit may typically have an overall diameter from 1.0 mm to 8.0 mm, preferably from 2.2 mm to 6.8 mm, and more preferably from 3.4 mm to 5.6 mm. For each land, the land leading edge region 11 and the trailing edge region 12 may typically have an average radius of at least 0.5 mm and at most 4.0 mm.

An opening angle φ (phi) of the flute 5s is determined between two diametrical reference lines RL1 and RL2, which are radial, i.e., situated in one and the same plane perpendicular to the center axis A, with RL1 extending between the leading edge region 11 and center axis A and RL2 extending between the trailing edge region 12 and the center axis A. The opening angle φ may range from 91° to 179°, preferably 125° to 170°, and more preferably 140° to 155°.

Figure 6A:
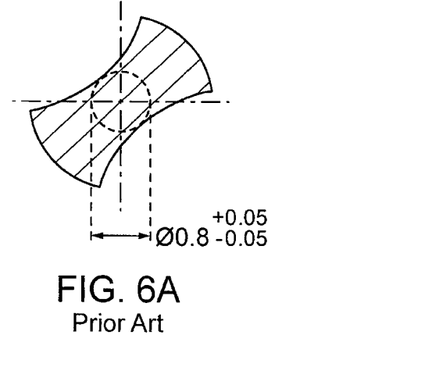
FIGS. 6A-6E show cross-sections of various prior art drills.
Figure 6B:
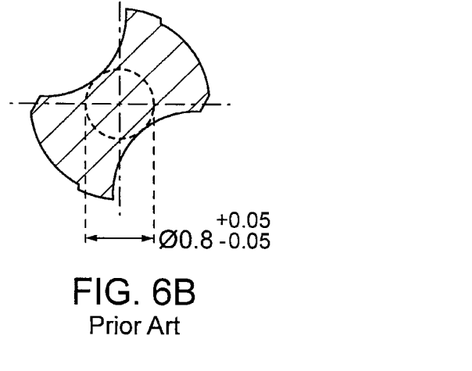
Figure 6C:
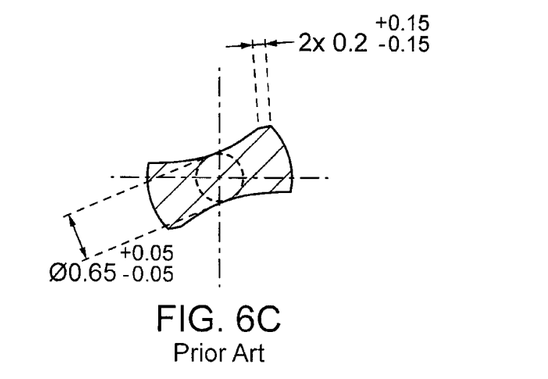
Figure 6D:
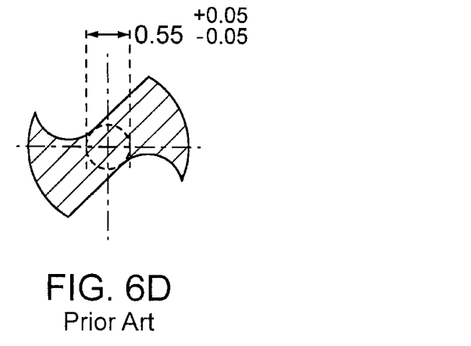
Figure 6E:
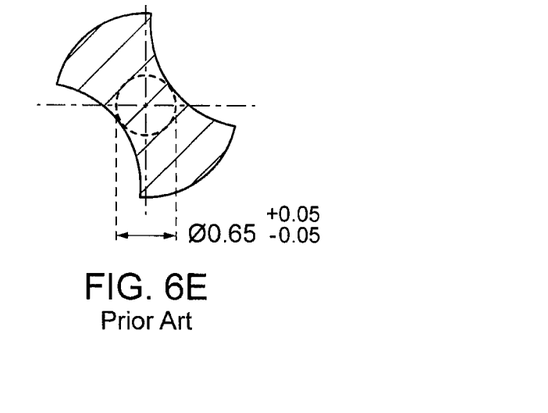
Figure 7A:
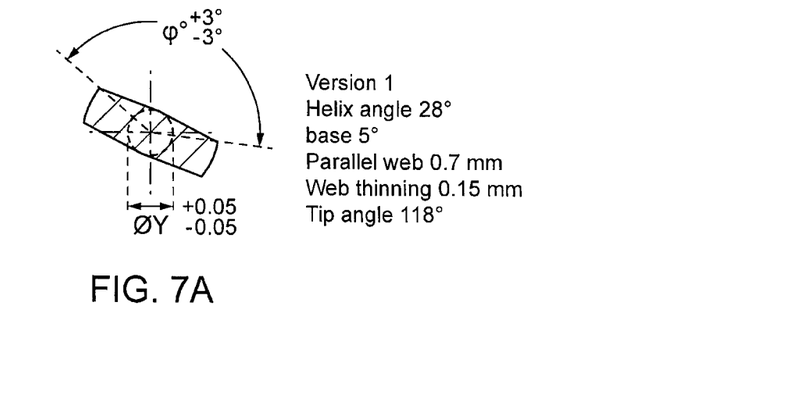
FIG. 7A is a cross-sectional view of a forth embodiment of the present invention.
Figure 7B:
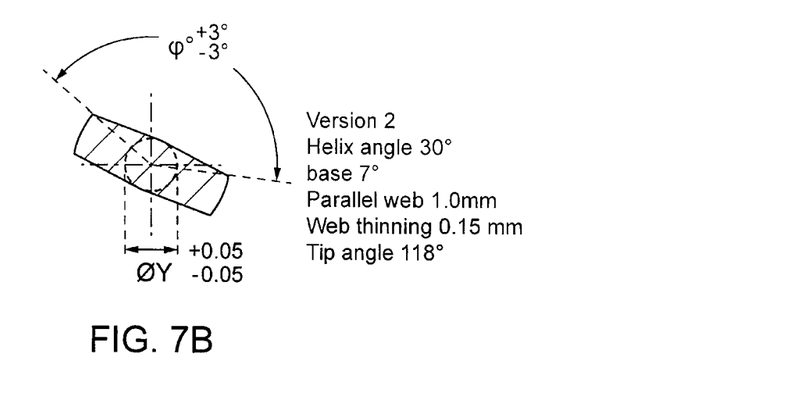
FIG. 7B is a cross-sectional view of a fifth embodiment of the present invention.
Figure 8A:
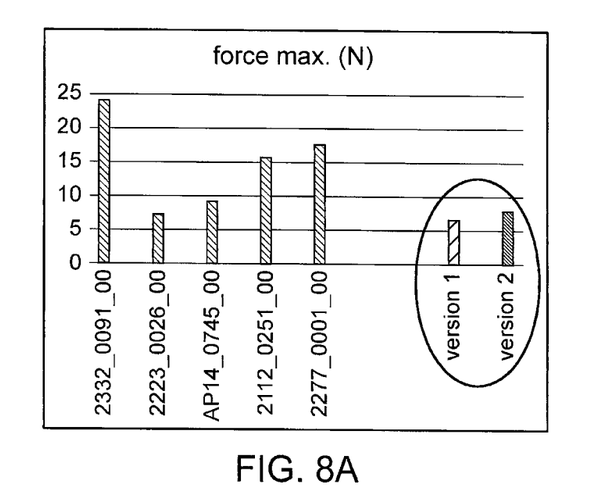
FIG. 8A is a chart comparing Max Force of the drills shown in FIGS. 6A-7B.
Figure 8B:
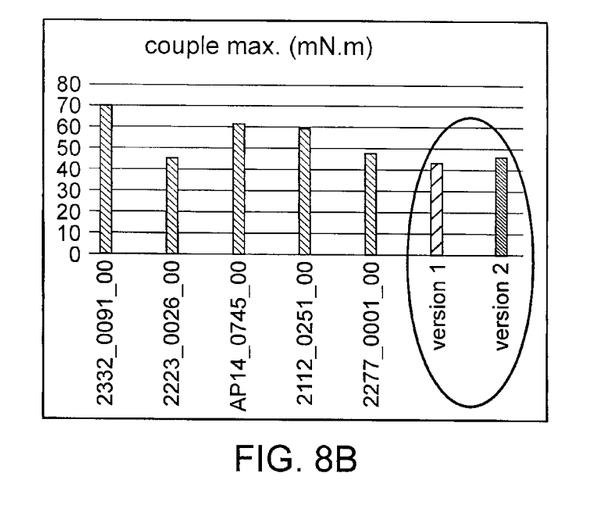
FIG. 8B is a chart comparing Max Torque of the drills shown in FIGS. 6A-7B.
Figure 9:
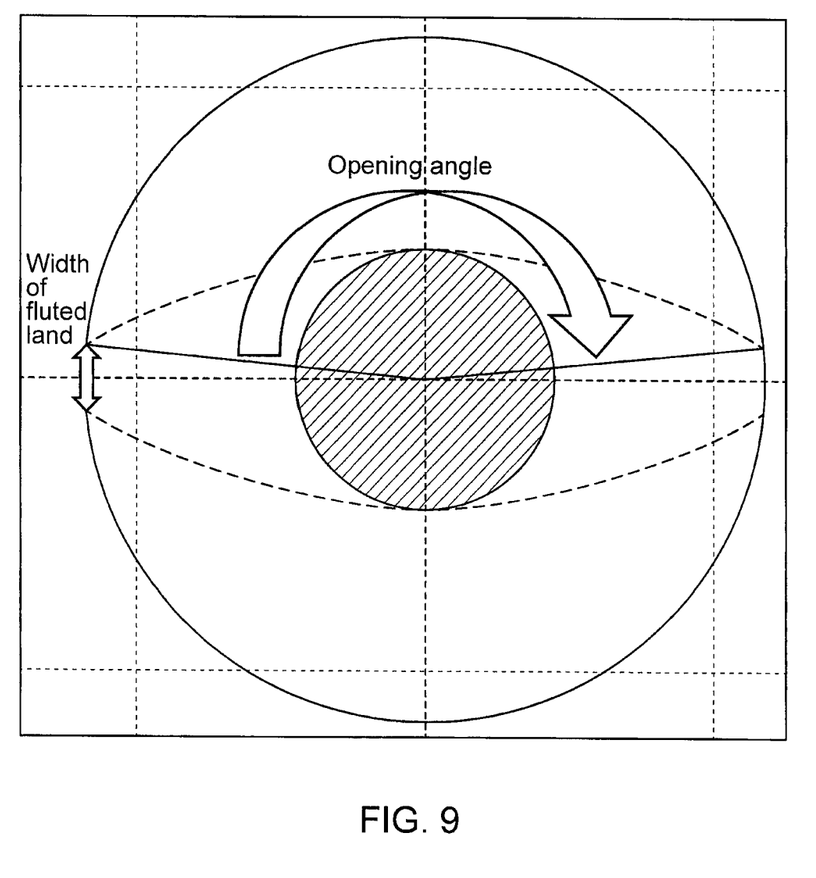
FIG. 9 shows an opening angle representation of a cross-section of a sixth embodiment of the present invention.
Figure 10A:
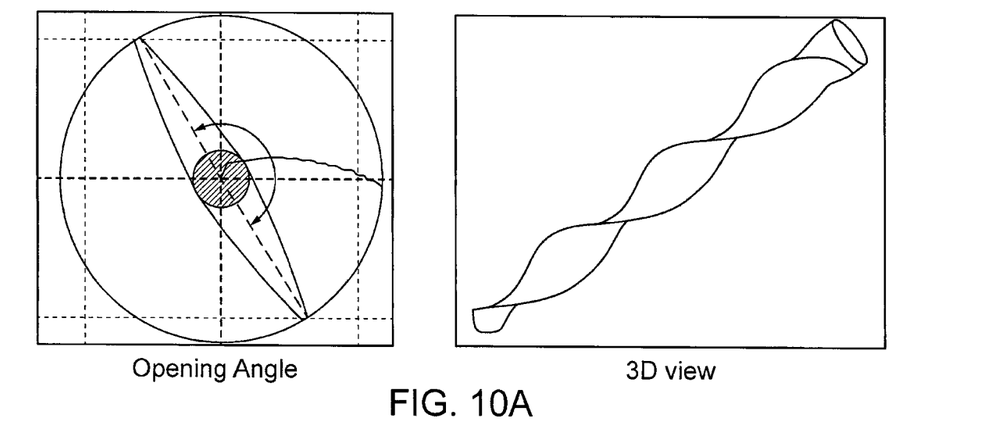
FIGS. 10A-10D show additional embodiments of the present invention.
Figure 10B:
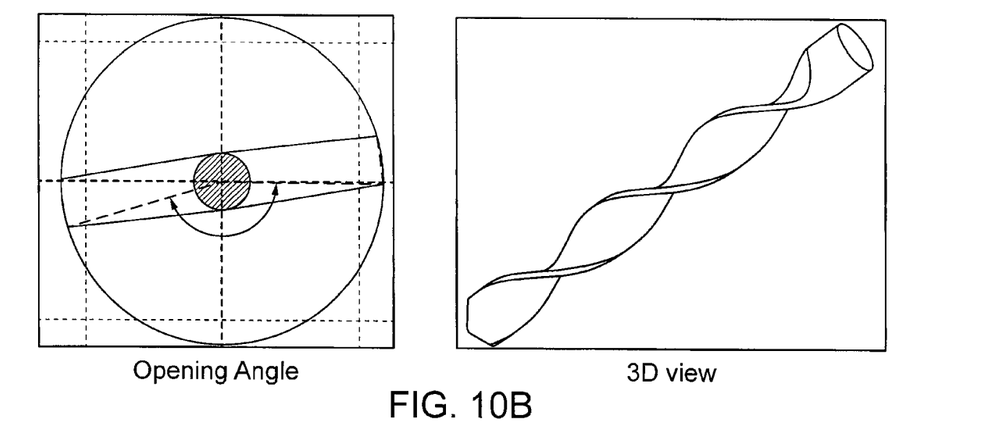
Figure 10C:
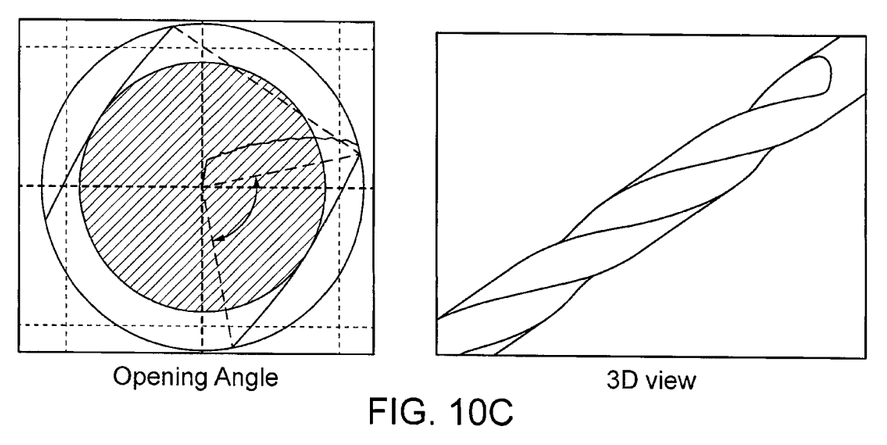
Figure 10D:
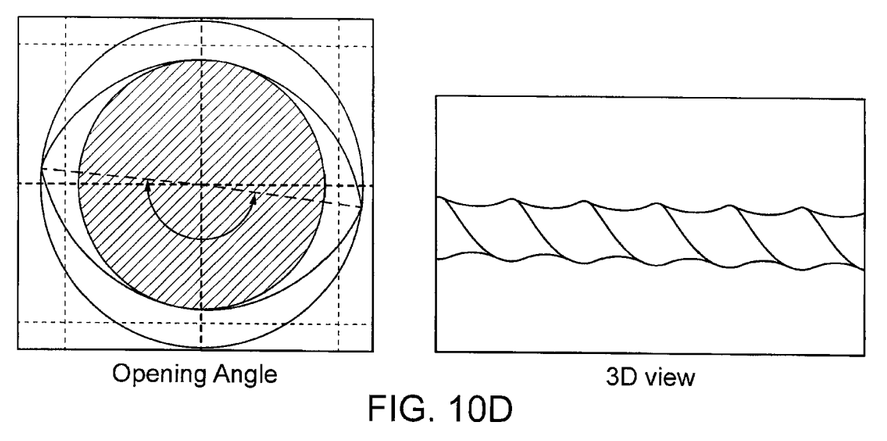
Figure 11A:
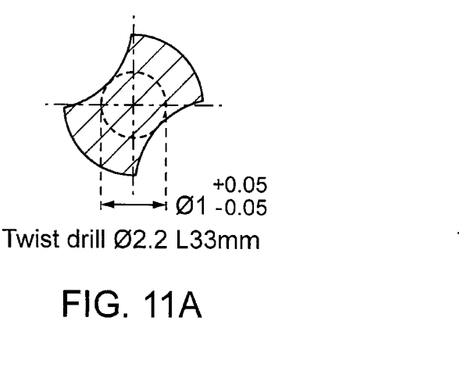
FIG. 11A is a cross-sectional view of a prior art twist drill having an opening angle phi of 2.2.
Figure 11B:
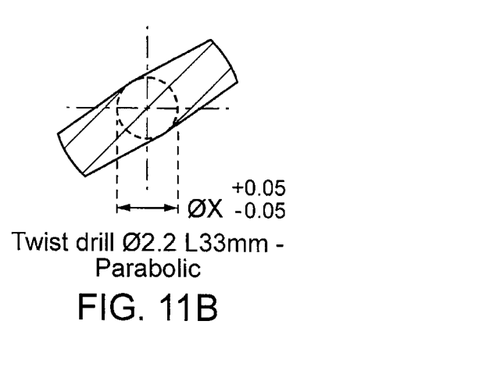
FIG. 11B is a cross-sectional view of a Parabolic twist drill of the present invention having an opening angle phi of 2.2.
Figure 11C:
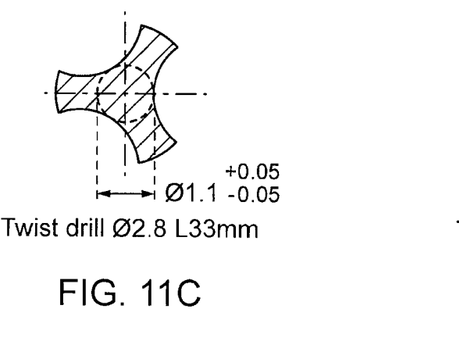
FIG. 11C is a cross-sectional view of a prior art twist drill having an opening angle phi of 2.8.
Figure 11D:
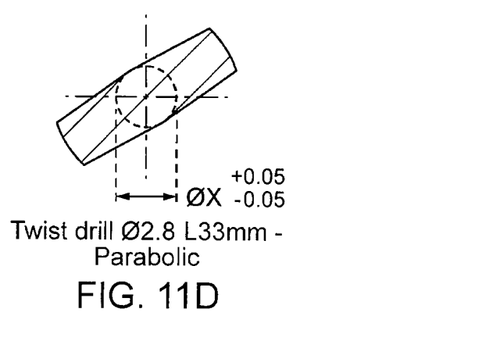
FIG. 11D is a cross-sectional view of a Parabolic twist drill of the present invention having an opening angle phi of 2.8.
Figure 11E:
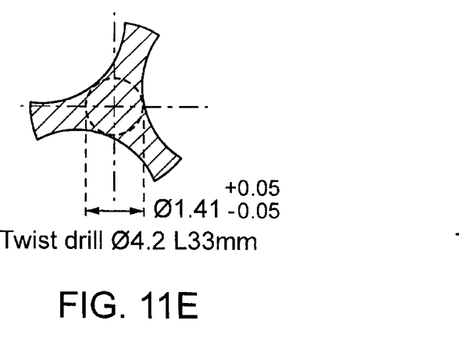
FIG. 11E is a cross-sectional view of a prior art twist drill having an opening angle phi of 4.2.
Figure 11F:
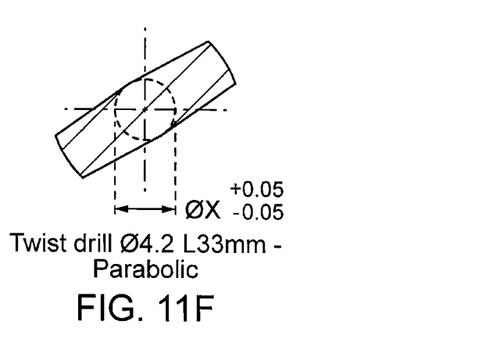
FIG. 11F is a cross-sectional view of a Parabolic twist drill of the present invention having an opening angle phi of 4.2.
Figure 12A:
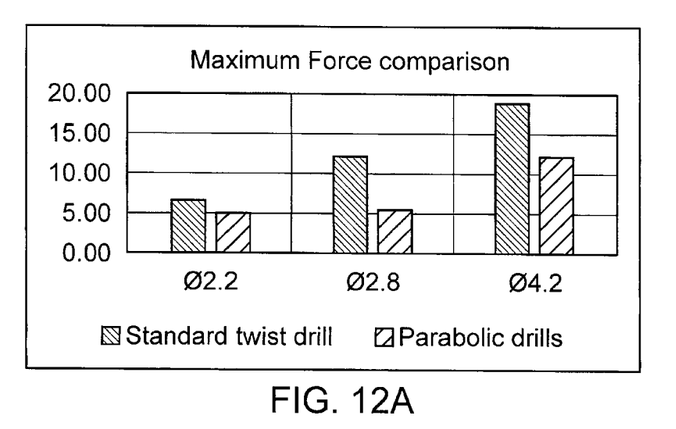
FIG. 12A is a chart comparing Max Force of the drills shown in FIGS. 11A-11F.
Figure 12B:
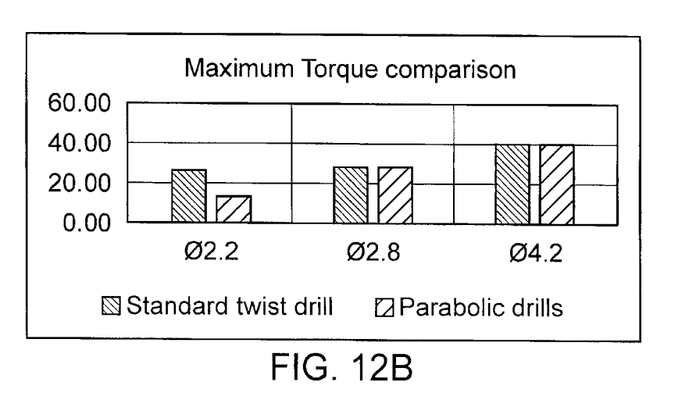
FIG. 12B is a chart comparing Max Torque of the drills shown in FIGS. 11A-11F.
Figure 12C:
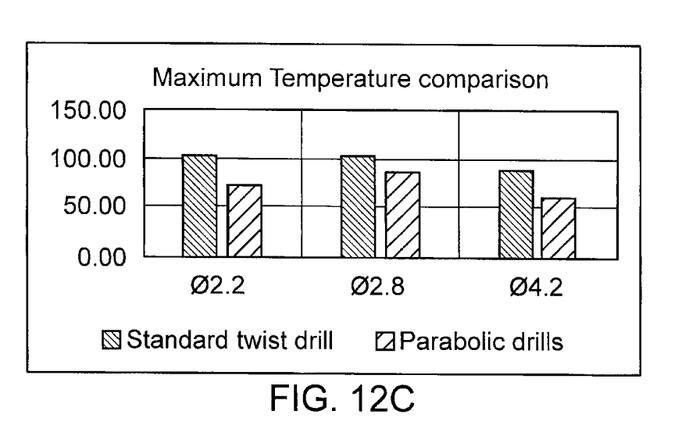
FIG. 12C is a chart comparing Max Temperature of the drills shown in FIGS. 11A-11F.

The opening angle is directly correlated to the shape of the core. It allows to build and determine the shape of the core. If the opening angle is not between 90° and 178°, you will have a flat core, a U section (FIGS. 6A-6C and 6E) or a J section (FIG. 6D). The fast helix angle will allow to facilitate the bone chips removing and allow to improve the bending resistance of the drill. Without this fast helix angle, it may be difficult to achieve improved characteristics with a reduced core. Both (fast helix angle and/or opening angle) allows for the reduction of the width of the fluted lands.

The land margin 10 constitutes a part cylindrical portion of the land 9 which is not ground away from the cylindrical shaft (shank 4) from which the drill bit 1 is formed. The land margin 10 has a width W (measured in a cross-sectional plane relative to the axis A) of at least 0.03 mm, preferably at least 0.4 mm, and more preferably at least 0.7 mm. Furthermore, it is appreciated that each land margin 10 may typically have an average width W of at most 1.8 mm, preferably at most 1.5 mm, and more preferably at most 1.2 mm. For example, each land margin 10 may typically have an average width W typically ranging from 0.03 mm to 1.8 mm, preferably from 0.4 mm to 1.5 mm, and more preferably from 0.7 mm to 1.2 mm. The land margins 10 each lie on a circle B extending about the central axis A and having a diameter equal to the overall diameter of the drill bit (being generally equal to the diameter of the shank 4 in the embodiment depicted). The width W may be the same or different for each land margin 10.

In one preferred embodiment, the width W of land margins 10 may be less than the thickness T of the core 13, taken in a cross-sectional plane extending perpendicular to the central axis A.

The tapered cutting end part 2 may be of a conventional configuration. Alternatively, the cutting end part 2 may advantageously be of either of the specific forms depicted in the accompanying drawings.

The bench test that was used during the tests shown in FIGS. 6A-8B and FIGS. 11A-11F (with FIGS. 6A-6E, 11A, 11C, and 11E being cross-sections of prior art drills and FIGS. 7A-7B, 11B, 11D, and 11F being cross-sections of Parabolic drills of the present invention) were enslaved by feed rate, it means that the feed rate remains constant during the drilling. Generally, Torque and load are recorded during the drilling and the speed rotation is around 800 rpm. FIGS, 8A-8B and 12A-12C show charts representing the data provided in FIGS. 6A-8B and 11A-11F.

Advantageously, the convex web design of the present invention may reduce the thermal effect associated with instruments/drills of the prior art. The thermal effect is the heat generated from the metal-bone interface during bone processing in surgical operations. The heat generated during drilling occurs due to the friction of the cutting tool to the work piece interface and transforming the applied cutting energy into heat energy that causes necrosis and combustion of bone tissue.

Drilling operation during bone implantation and thermal damages were investigated and it was observed that the drill force caused an increase in temperature (For example the drill force is increased when the drill blocks during the drilling because the bone chips are not correctly removed (friction) or when the cutting edges are damaged).

It is believed that with increased thermal effect, the risk of osteonecrosis will be higher, which could result in the osteo-integration of the implant being compromised.

The drill bits described above will typically be formed of stainless steel when configured for use as a dental/medical drill bit, but other suitable high strength metallic materials may be utilized as desired to suit various applications.

The invention claimed is:

1. A parabolic instrument comprising a shank, a working portion, and a tip portion, the working portion having a core, and a plurality of flutes being defined by at least two lands having a land margin; wherein an entire length of the working portion has a same parabolic cross-section formed by opposing convexed surfaces extending between at least two opposing land margins, wherein a first convexed surface of the opposing convexed surfaces extends from the core at a first flute base to a first land margin along a first flute leading side wall and to a second land margin along a first flute trailing wall and wherein a second convexed surface of the opposing convexed surfaces extends from the core at a second flute base to the first land margin along a second flute trailing side wall and to the second land margin along a second flute leading wall; wherein the at least two lands have a diameter d substantially equal to an overall diameter D of the shank, and wherein each land margin is defined by a width W and the core is defined by a thickness T that extends between the first flute base and the opposing second flute base so that the width W of at the at least two opposing land margin are smaller than the thickness T of the core.

2. The instrument of claim 1, wherein the width W ranges from 0.03 mm to 1.8 mm.

3. The instrument of claim 2, wherein the thickness T ranges from about 0.1 mm to about 2.0 mm.

4. The instrument of claim 1, wherein at least one of the plurality of flutes include a helical angle ranging from about 15° to about 50°.

5. The instrument of claim 1, wherein each of the plurality of flutes include a helical angle ranging from about 15° to about 50°.

6. The instrument of claim 1, further comprising an opening angle φ of the plurality of flutes ranging from 91° to 179°., the opening angle φ is determined between two diametrical reference lines RL1 and RL2, which are situated in one and the same plane perpendicular to a center axis A, with RL1 extending between a leading edge region of a first land and the center axis A and RL2 extending between a trailing edge region of a second land and the center axis A.

7. The instrument of claim 1, wherein the instrument is an implant drill.

8. The instrument of claim 1, wherein the first flute base opposes the second flute base about the core of the working portion.

9. The instrument of claim 1, wherein the thickness T of the core is substantially the same along the working portion between the shank and the tip portion.

10. The parabolic instrument according to claim 1, wherein each trailing side wall and each leading side wall define a generally straight side wall segment such that taken with the base form a generally convex cross-section.

11. A parabolic instrument comprising:
   a shank;
   a working portion having a core and a plurality of flutes being defined by at least two lands having a land margin;
   an opening angle φ of the plurality of flutes ranging from 91° 179°, the opening angle φ is determined between two diametrical reference lines RL1 and RL2, which are situated in one and the same plane perpendicular to a center axis A, with RL1 extending between a leading edge region of a first land and the center axis A and RL2 extending between a trailing edge region of a second land and the center axis A; and
   a tip portion;
   wherein an entire length of the working portion has a same parabolic cross-section formed by opposing convexed surfaces extending between at least two opposing land margins;
   wherein a first convexed surface of the opposing convexed surfaces extends from the core at a first flute base to a first land margin along a first flute leading side wall and to a second land margin along a first flute trailing wall and wherein a second convexed surface of the opposing convexed surfaces extends from the core at a second flute base to the first land margin along a second flute trailing side wall and to the second land margin along a second flute wall;
   wherein the at least two lands have a diameter d substantially equal to an overall diameter D of the shank,
   wherein each land margin is defined by a width W and the core is defined by a thickness T that extends between the first flute base and the opposing second flute base so that the width W of at the at least two opposing land margins are smaller than the thickness T of the core;
   wherein the width W ranges from 0.03 mm to 1.8 mm;
   wherein the thickness T ranges from about 0.1 mm to about 2.0 mm;
   wherein at least one of the plurality of flutes include a helical angle ranging from about 15° to about 50°; and
   wherein the thickness T of the core is substantially the same along the working portion between the shank and the tip portion.

12. The parabolic instrument according to claim 11, wherein each trailing side wall and each leading side wall define a generally straight side wall segment such that taken with the base form a generally convex cross-section.

* * * * *